(12) United States Patent
Tanaka et al.

(10) Patent No.: US 6,391,018 B1
(45) Date of Patent: May 21, 2002

(54) CATHETER

(75) Inventors: Nobuhiko Tanaka; Ichizou Ohkata, both of Yokohama (JP)

(73) Assignee: Piolax Medical Devices, Inc., Kanagawa-ken (JP)

( * ) Notice: Subject to any disclaimer, the term of this patent is extended or adjusted under 35 U.S.C. 154(b) by 0 days.

(21) Appl. No.: 09/471,856

(22) Filed: Dec. 23, 1999

(30) Foreign Application Priority Data

Dec. 24, 1998 (JP) ............................................. 10-367303

(51) Int. Cl.⁷ ............................................... A61M 25/00
(52) U.S. Cl. ................................... 604/524; 604/164.13
(58) Field of Search ............................... 604/524, 93.01, 604/104, 107, 164.03, 164.13, 264, 523, 526, 527, 530, 532; 606/191, 194

(56) References Cited

U.S. PATENT DOCUMENTS 4,790,624 A  12/1988 Van Hoye et al.
5,084,015 A * 1/1992 Moriuchi .................... 604/185
5,554,139 A * 9/1996 Okajima ..................... 600/433
5,709,874 A  1/1998 Hanson et al.
5,730,741 A  3/1998 Horzewski et al.
6,074,378 A * 6/2000 Mouri et al. ................ 604/264

FOREIGN PATENT DOCUMENTS

WO  9835717  8/1998

OTHER PUBLICATIONS

Certified copy of Japanese patent dated Dec. 24, 1998.
Copy of Japanese patent abstract for 10-272187.

* cited by examiner

*Primary Examiner*—Teresa Walberg
*Assistant Examiner*—Vinod D. Patel
(74) *Attorney, Agent, or Firm*—Howard & Howard

(57) ABSTRACT

The catheter of the present invention includes a tube-shaped catheter main body, a shaping member provided at least at the front end portion of the catheter main body such that the shaping member can impart a winding shape to the front end portion of the catheter, and a cavity portion formed at the inner side of the shaping member.

11 Claims, 6 Drawing Sheets

CATHETER

BACKGROUND OF THE INVENTION

The present invention relates to a catheter, and more specifically, a catheter which can be continuously or temporarily retained inside a blood vessel or the like of a patient so that medication liquid such as carcinostatic substance can be injected in an appropriate manner.

Conventionally, when medication liquid such as a carcinostatic substance is to be dosed to a patient, the medication liquid is generally injected into a blood vessel of the patient's body by using a syringe or an instillator. However, in this conventional method, there is a problem that the medication liquid affects not only cancer cells but also normal cells because the liquid is circulated throughout the body through the blood vessels.

Therefore, there has been an attempt to insert a catheter into a blood vessel through the skin and the front end of the catheter is located at the inlet position of the arterial canal extending to an internal organ having cancer, so that the medication liquid is directly injected into the internal organ having the cancer and a significant carcinostatic effect is achieved with a relatively small amount of dose.

In this attempt, after the catheter has been inserted into the patient's body such that the front end of the catheter is located at the inlet position of the arterial canal extending to the targeted internal organ, the base portion side of the catheter is fixed on the patient's body so that the front end of the catheter should not move from the determined inlet position during the injection of the medication liquid.

However, in this conventional method, although the base portion side of the catheter is fixed on the patient's body, the front end portion of the catheter could move from the determined position during the injection due to, for example, movement of patient's body during sleep, resulting in flow of the medication liquid to some internal organs other than the targeted one.

In order to overcome such problems, Japanese Patent Application, Laid-Open Publication No. 10-272187 proposes a catheter in which a wire material having elasticity and a curved shape is provided at the front end inner peripheral portion of the tube-shaped catheter main body so that the front end portion of the catheter main body has a curved shape and this curve-shaped front end portion of the catheter is pressingly fixed on the wall of the blood vessel.

SUMMARY OF THE INVENTION

However, in the case of the catheter disclosed in Japanese Patent Application Laid-Open Publication No. 10-272187, as the wire material is inserted at the front end portion of the catheter main body, the flow of the medication liquid is disturbed at that portion. In addition, it is not possible to put a guide wire through the front end portion for the same reason.

Accordingly, when the catheter disclosed in Japanese Patent Application Laid-Open Publication No. 10-272187 is to be inserted into the blood vessel, the following steps are required: 1) a guide wire is inserted first and its from end is disposed at the targeted position; 2) a parent catheter is inserted along the outer periphery of the guide wire; 3) the guide wire is pulled out when the front end of the patent catheter reaches the targeted position; 4) and the catheter for dosing the medication liquid is inserted through the parent catheter.

As a result, complicated and time-consuming work is required for inserting the catheter for dosing the medication liquid. In addition, there arises another problem, an insertion portion which is larger than the sectional area of the catheter for dosing the medication liquid has to be created on the patient's body because the parent catheter has a larger diameter than the catheter for dosing the medication liquid.

The present invention solves the aforementioned problems observed in use of the conventional catheter. An object of the present invention is to provide a catheter which can be continuously or temporarily retained in a blood vessel or the like of a patient's body and which requires only a quick and simple operation for insertion and a relatively small insertion portion.

The catheter of the present invention includes a tube-shaped catheter main body, a shaping member which is provided at least at the front end portion of the catheter main body for imparting a winding shape to the front end portion of the catheter, and a cavity portion formed at the inner side of the shaping member.

Due to the structure described above, a guide wire can be very easily inserted through the cavity portion of the catheter. Specifically, the guide wire is first inserted into a blood vessel or the like of a subject and the front end portion of the guide wire is disposed at the targeted site. The catheter is then inserted along the outer periphery of the guide wire. Accordingly, the catheter can reliably be disposed at the targeted position.

When the catheter is disposed at the targeted site, or more specifically, when the front end portion of the catheter has reached the front end portion of the guide wire, the guide wire is pulled out so that the front end portion of the catheter restores its winding shape.

The catheter can be then retained, in such a state, continuously or temporarily in the patient's body, so that the medication liquid is reliably dosed to the targeted portion of the subject (the patient's body) through the catheter retained in such a manner.

Accordingly, the catheter can be inserted directly into the patient's body without using a parent catheter. As a result, only a simple and quick operation in a relatively small insertion portion is necessitated for insertion of the catheter.

The winding front end portion of the catheter preferably has a spiral structure, such that the front end portion of the catheter can be reliably pressed and fixed on the inner periphery of the blood vessel.

In addition, the shaping member is formed preferably of a super elastic material so that the shaping member easily takes on a linear shape when the guide wire is inserted and restores the winding shape when the guide wire is pulled out.

Specifically, such a elastic material preferably containing at least one of the following alloys including Ni—Ti alloy, Cu—Zn—X alloy (X=Al or Fe) and Ni—Ti—X (X=Fe, Cu, V or Co).

In addition, the shaping member is preferably constructed as a coil, so that the cavity portion can be reliably secured and thus the guide wire can be inserted smoothly.

Further, the coil, preferably has a flat portion on the cavity portion side, so that the cavity portion can be more reliably secured and thus the guide wire can be inserted more smoothly.

The shaping member preferably has a double-leave in structure when imparting a winding shape to the front end portion of the catheter main body, so that the cavity portion can be reliably secured.

Alternatively, the shaping member may be structured as a mesh tube.

Further, in the front end of the catheter main body, the peripheral wall of the portion to which a winding shape is imparted by the shaping member is preferably provided with holes so that the medication liquid flows out through the holes. More specifically, the winding shape is a spiral shape and the holes are formed at the inner side of the spiral shape so that the medication liquid is not directly injected onto the blood vessel of the subject.

The winding shape preferably has a diameter which is larger than the diameter of the retention site of the subject, so that the front end portion is reliably retained at the retention site.

DETAILED DESCRIPTION OF THE PREFERRED EMBODIMENT

Figure 1:
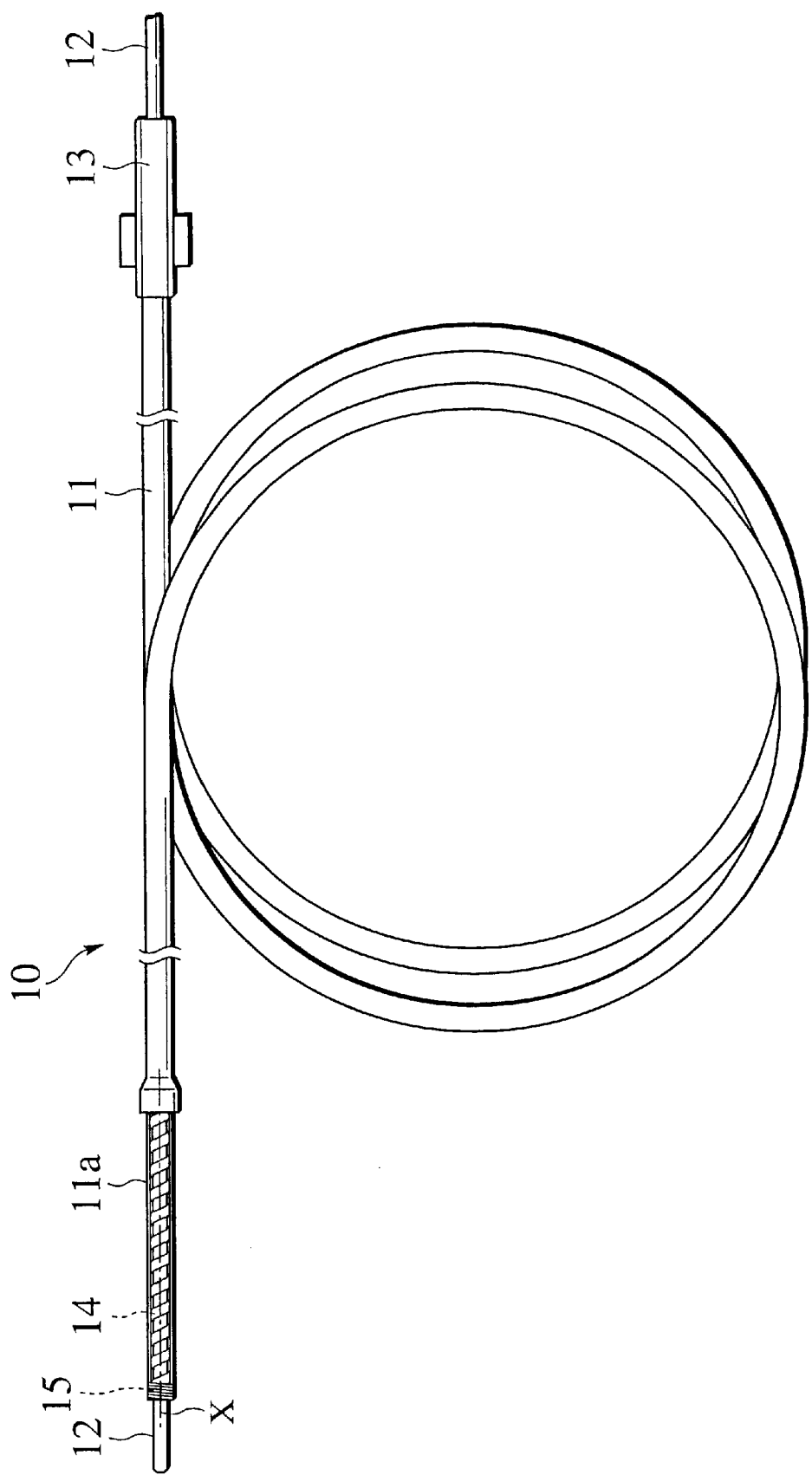
FIG. 1 is a side view of a catheter in which the front end portion of the catheter is shown as a partial sectional view.
Figure 2:
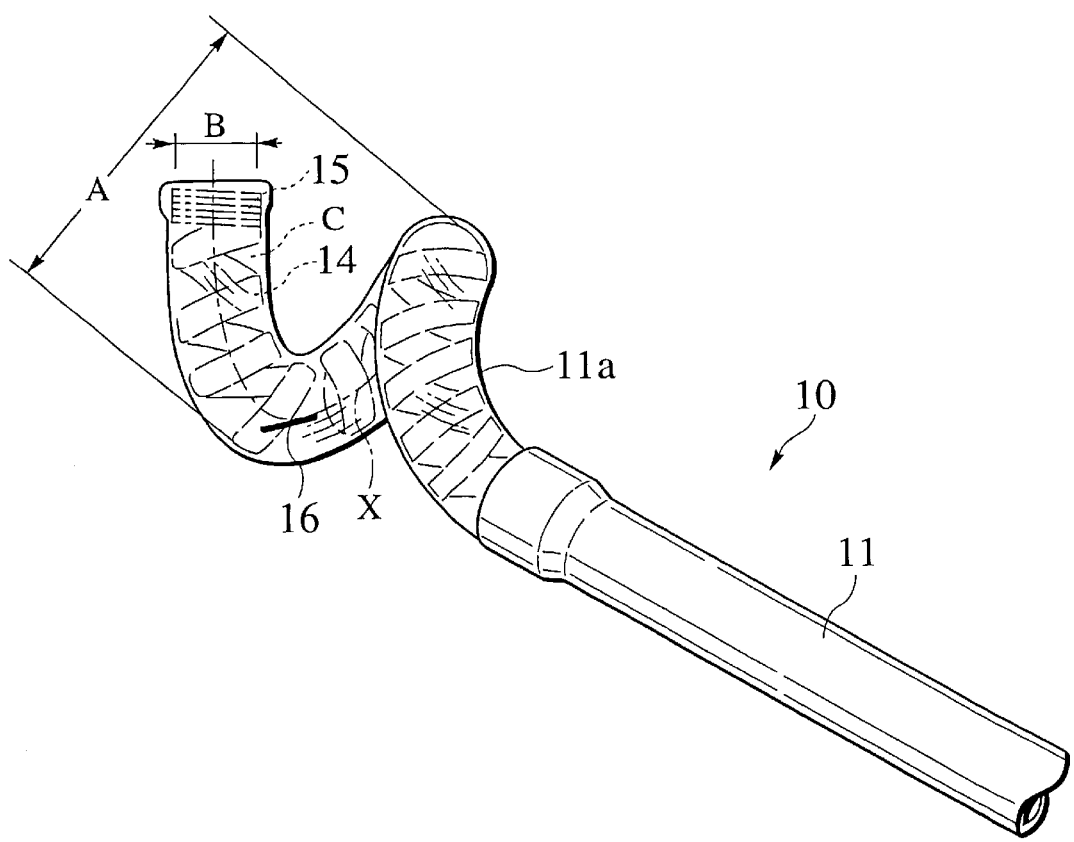
FIG. 2 is a perspective view of the front end portion of the catheter, in which view the inside of the front end portion is illustrated by phantom lines.
Figure 3:
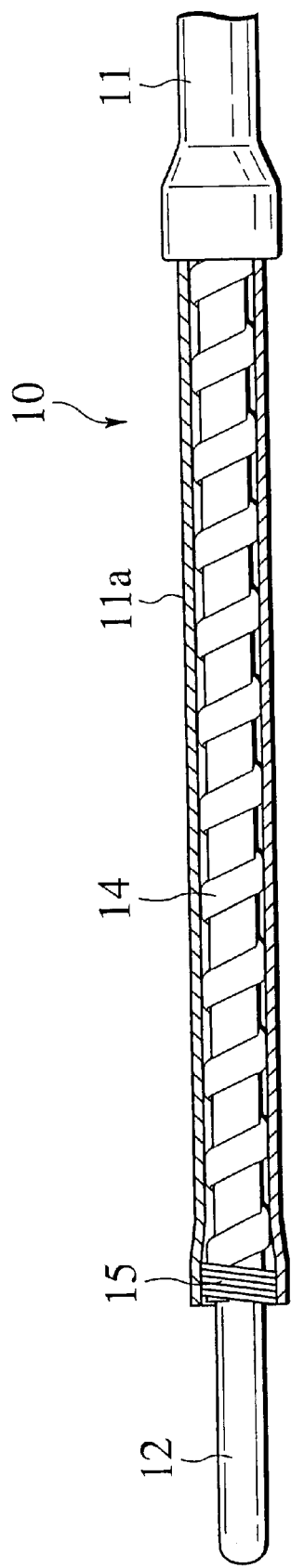
FIG. 3 is a side view of the catheter in which the front end portion of the catheter is shown as a partial sectional view.

Hereinafter, a preferred embodiment of the present invention will be described in detail with reference to FIGS. 1 to 7.

A catheter 10 has a tube-shaped catheter main body 11 which is made of a synthetic resin such as urethane, nylon, polyethylene, polypropylene, silicone or a shape memory alloy or the like. A plug body 13 is provided at the base end portion of the catheter main body 11 such that the plug body 13 is inserted along a guide wire 12 while sealing the guide wire 12.

The inner periphery of the catheter main body 11 is preferably coated with a hydrophilic resin, so that the guide wire 12 can be slid against the catheter main body 11 more smoothly. The outer periphery of the catheter main body is preferably coated with a hydrophilic resin to allow the catheter main body 11 to be slid against the inner wall of a blood vessel or the like more smoothly.

A tube 11a made of a material which is more flexible than the catheter main body 11 is connected to the front end portion of the catheter main body 11. In the present embodiment, the base end of the tube 11a is inserted into the inner periphery of the front end portion of the main body 11 and connected thereto by adhesion or welding. The tube 11a substantially forms the front end portion of the catheter main body 11. As the front end portion of the catheter main body 11 essentially constitutes the flexible tube 11a, the front end portion easily restores a winding shape by a shaping member which will be described later. In addition, the catheter main body 11 as a whole may be formed of the same material as the tube 11a.

A coil 14 of flat wire made from a super elastic material which will be described later is provided at the inner periphery of the tube 11a. The coil 14 has what is called a double helical structure in which the flat wire forms a helix (the primary helix) and the primary helix then spirals to form a larger helix (the secondary helix). As a result, at a no-load state in which no load is acting on the tube 11a by the guide wire 12 and the like, the tube 11a portion of the catheter main body 11 is imparted a spiral shape by the double helical coil 14. In addition, in the present embodiment, as the coil 14 constitutes a flat wire provided along the inner periphery of the tube 11a portion of the catheter main body 11 such that an inner cavity C is secured along the center axis X of the coil 14. The guide wire 12 can very easily be inserted through the catheter main body 11, as shown in FIG. 1 and FIGS. 4A to 4C. The coil 14 serves as a shaping member in the present embodiment.

In the present embodiment, the coil 14 is formed of super elastic material which has been processed so that the material has a shape-memory property and super elasticity in a temperature range similar to that of the human body. Alternatively, however, the coil 14 may be formed of other materials such as a metal wire (stainless steel and the like) and a FRP wire material having a high rigidity.

The examples of a suitable super elastic material, such as, Ni—Ti alloy, Cu—Zn—X (X=Al, Fe or the like) alloy, Ni—Ti—X (X=Fe, Cu, V, Co or the like) may be utilized by the invention. Ni—Ti alloys are known to show a shape memory effect and a super elasticity (pseudoelasticity) effect as a shape memory alloy. Among such alloys, in the case of that which shows a super elasticity (pseudoelasticity) effect, even if a distortion load which exceeds the yield point of the alloy is applied to the alloy, the alloy restores its original shape without showing permanent deformation when the load is removed, thereby providing excellent restoration properties against twisting and bending as well. The alloy of this type is distinctively different from ordinary metal materials which are permanently deformed when a distortion load which exceeds the yield point of the metal materials is applied thereto. Thus, the alloys showing a super elasticity effect (pseudoelasticity) are suitable as material for the shaping member. It is further preferable to employ the alloys of which super elasticity (pseudoelasticity) effect has been controlled such that the effect is demonstrated at a temperature which is no higher than human or animal body temperature.

The wire material which forms the coil 14 may be an ordinary round wire. However, a flat wire, preferably with a plate-like cross section is utilized by the present invention. A wire material having a hemispheric section may also be used so that the flat surface faces the inner side of the coil 14. In a case in which the coil 14 is formed by a flat wire or a wire material which has a flat surface facing the inside of the coil 14, the inner cavity is more reliably secured along the center axis of the coil 14 and thus the guide wire 12 can be more smoothly inserted through the coil.

The outer diameter A (the diameter of the secondary hole) of the coil 14 when no load is acting on the coil 14 is designed to be larger than the inner diameter of the retention site of the blood vessel or the like, so that the tube 11a has a coil-like winding shape having an outer diameter which is larger than the inner diameter of the retention site. Accordingly, when the front end portion of the catheter 10 is left in a state in which no external force is acting thereon, the coil 14 restores the coil-like shape so that the coil 14 is pressed on the inner wall of the retention site and the front end portion of the catheter 10 is fixed at the retention site.

Further, the inner diameter B of the inner cavity C along the center axis X of the coil 14 is designed to be larger than the outer diameter of the guide wire 12 so that the guide wire 12 can be put through the coil 14. When the guide wire 12 is inserted through the inner cavity c along the center axis x of the coil 14, the secondary helix of the coil 14 is made straight due to the rigidity of the guide wire 12 and maintained in such a linear state as shown in FIG. 1.

A ring-shaped contrast chip 15 made of a closely-contacting coil is provided on the inner periphery of the front end portion of the tube 11a. Suitable materials for the contrast chip 15, do not allow penetration of X rays such as gold, platinum, silver, bismuth, tungsten or other alloys with similar properties.

Further, at least one medication liquid flowing hole 16 is provided at a site or at a plurality of sites of the peripheral inner wall of the tube 11a. Here, the medication liquid flowing hole(s) 16 is preferably located at a portion which is the inner side of the secondary helix when the tube 11a has restored the spiral shape of the secondary helix by the coil 14. In this arrangement, the medication liquid is prevented from being injected directly on the inner wall of the blood vessel or the like and thus prevents damage to the inner wall of the blood vessel or the like.

Next, the process of dosing the medication liquid such as carcinostatic substance using the catheter 10 will be described with reference to FIGS. 4A to 7. In the drawings, the reference number 51 is designated to the skin and the reference number 52 is designated to a blood vessel.

Figure 5:
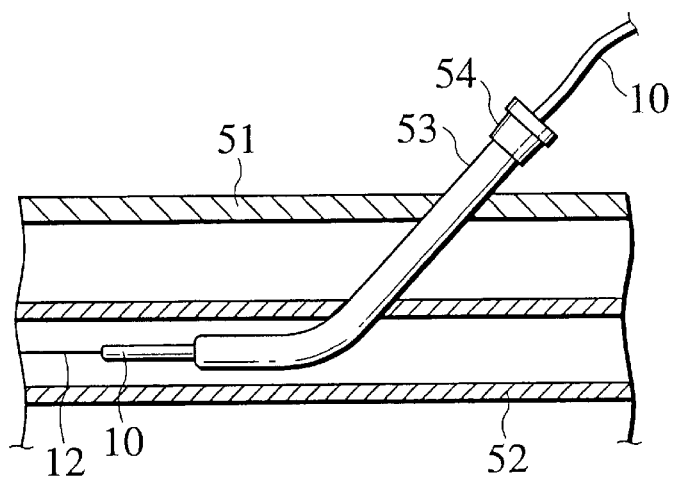
FIG. 5 is a view showing a state in which the catheter is being inserted into a blood vessel.

A sheath 53 is inserted into the blood vessel 52 via the skin 51 according to the known Seldinger technique as shown in FIG. 5.

Next, the guide wire 12 is inserted through a plug body 54 provided at the base end of the sheath 53 so that the front end of the guide wire 12 is disposed at the targeted site in the blood vessel 52, for example, a blood flow inlet position from which blood flows to the internal organ which has a cancer.

Thereafter, the catheter 10 is inserted so that the catheter 10 proceeds along the external periphery of the guide wire 12 until the front end of the catheter 10 reaches the front end of the guide wire 12.

Figure 4A:
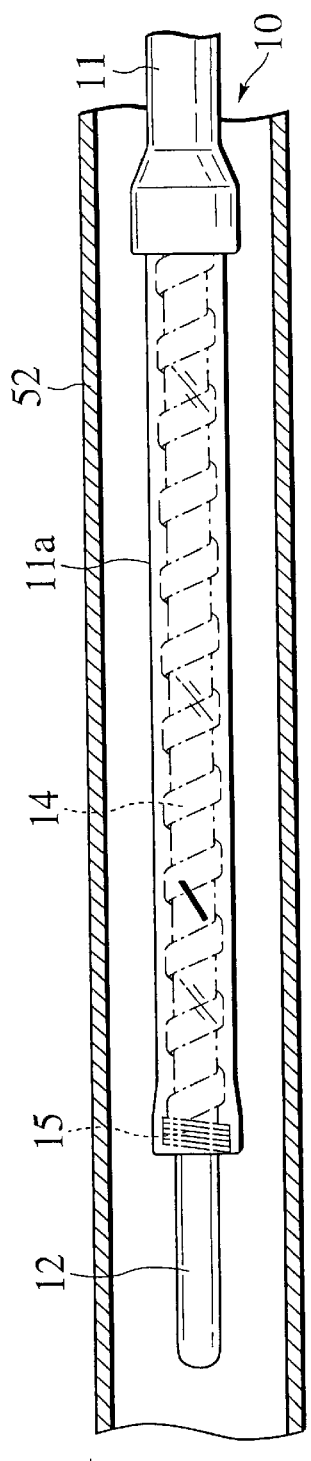
FIG. 4A is a view showing a state in which a guide wire has been inserted through the front end portion during a use of the catheter.
Figure 4B:
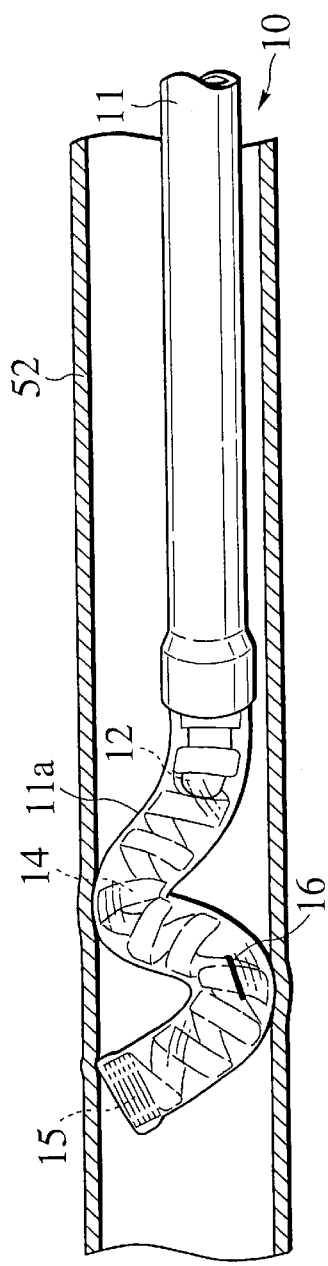
FIG. 4B is a view showing a state in which the guide wire which has been inserted through the front end portion is being gradually pulled out during a use of the catheter.
Figure 4C:
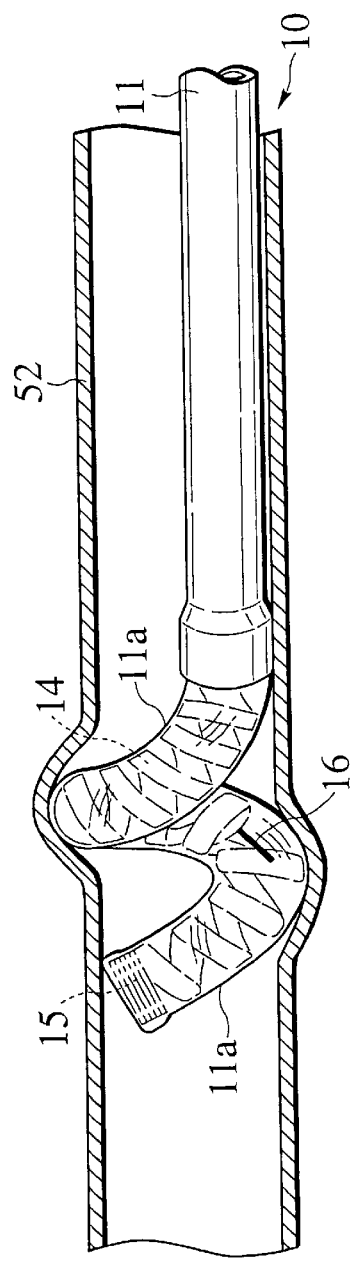
FIG. 4C is a view showing a state in which the guide wire which was inserted through the front end portion has been completely pulled out during a use of the catheter according to the embodiment.

At this stage, as shown in FIG. 4A, the front end portion of the catheter 10 has been extended so as to have a linear shape due to the rigidity of the guide wire 12 and can move in the blood vessel 52 relatively freely. Then, as shown in FIG. 4B, as the guide wire 12 is gradually pulled out, the front end portion of the catheter 10 begins to take on the spiral shape due to the restoration force of the coil 14 and thus the outer diameter of the front end portion of the catheter 10 becomes larger than the diameter of the blood vessel 52. As a result, the front end portion of the catheter 10 starts to be pressed on the inner wall of the blood vessel 52. Further, when the guide wire 12 has been completely pulled out, the coil 14 restores the double helical structure. Accordingly, the front end portion of the catheter 10 is pressingly fixed on the inner wall of the blood vessel 52. The front end portion of the catheter 10 has taken on a spiral shape of the possible maximum diameter. The position at which the front end portion of the catheter 10 is fixed can be checked by means of the contrast chip 15. If the front end portion of the catheter 10 is not disposed at the targeted position, the guide wire 12 may be inserted again so as to return the front end portion of the catheter 10 to the linear state, so that the fixing operation may be carried out again.

The front end of the catheter 10 is now disposed at the targeted site in the blood vessel (the inlet portion from which the blood flows to the internal organ having a cancer, for example). As the front end portion of the catheter 10 is reliably fixed inside the blood vessel 52 as described above, there is no possibility that the front end portion of the catheter 10 moves from the targeted site, even if the patient moves his/her body in an inappropriate manner. In this state, the front end opening portion of the catheter 10 may be blocked by any blocking member, so that the medication liquid flows out only from the medication liquid flowing hole(s) 16.

Figure 6:
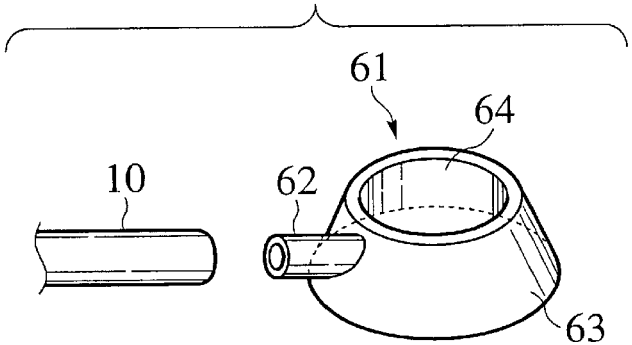
FIG. 6 is a view showing a state in which the catheter is about to be connected to a medication liquid injection port.

After the front end portion of the catheter 10 has been fixed at the targeted site and the guide wire 12 has been completely pulled out, the plug body 54 side of the sheath 53 is cut off so that the catheter 10 extends from the base portion of the sheath 53. Then, as shown in FIG. 6, the base portion of the catheter 10 which has been cut, as described above, is connected to the medication liquid flow outlet 62 of the medication liquid injection port 61. The medication liquid injection port 61 has a structure in which a rubber film 64 which can be penetrated by a syringe needle or the like is attached on the upper opening of a truncated-cone shaped container 63 made from synthetic resin having a hardness which does not allow penetration of a syringe needle or the like. The medication liquid flowing outlet 62 is provided in the inner wall of the container 63.

Figure 7:
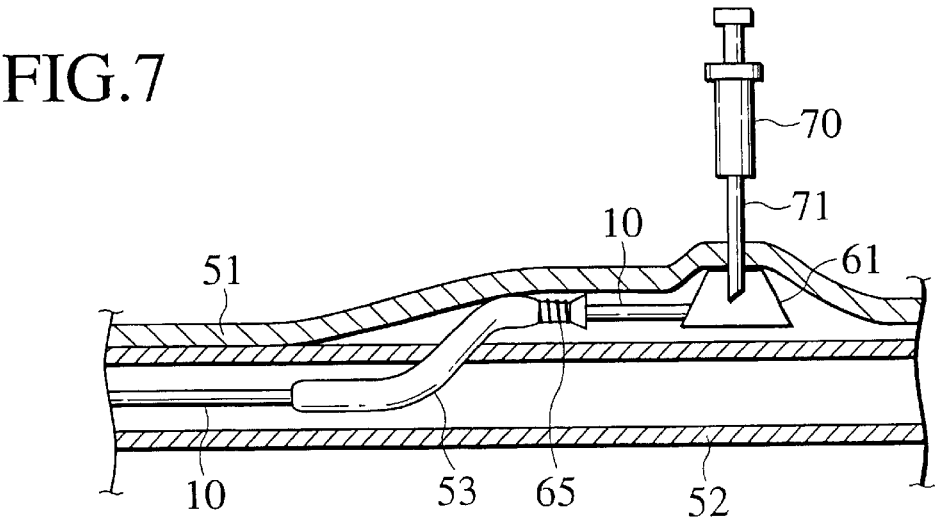
FIG. 7 is a view showing a state in which the catheter is retained in a patient's body.

Further, as shown in FIG. 7, the medication liquid injection port 61 is buried under the skin 51 by cutting the skin 51. The base portion of the sheath 53 which has been cut as described above is fixed on the catheter 10 by binding the sheath 53 on the catheter 10 with threads 65 or the like as shown in the drawing, so that the blood does not leak from that portion. In this state, the patient can live a normal daily life without having any restriction of movement. The front end of the catheter 10 is fixed at a specified site in the blood vessel 52 and does not move from the specified site during the use of the catheter 10 throughout the use of the catheter 10.

When the carcinostatic substance is to be dosed periodically, a needle 71 of a syringe 70 is inserted into the medication liquid injection port 61 through the skin 51 and the rubber film 64, so that the medication liquid in which the carcinostatic substance has been dissolved can be injected into the medication liquid port 61. The medication liquid flows through the medication liquid flowing outlet 62 and the catheter 10 and is discharged from the front end opening portion or the medication liquid flowing hole(s) 16 of the catheter 10. Accordingly, the carcinostatic substance can be selectively injected into the internal organ having a cancer. In addition, in a case in which the front end opening portion of the catheter 10 is blocked by the blocking member such that the medication liquid flows out mainly from the medication liquid flowing hole(s) 16, the medication liquid at first flows in the catheter 10 along the axis of the catheter 10 and then, after changing the flow direction, flows out in the transverse direction from the medication liquid flowing hole(s) 16 formed in the peripheral wall of the catheter 10. Due to this, the medication liquid is prevented from being injected harshly on the inner wall of the blood vessel and thus the inner wall of the blood vessel is less likely to get unnecessary stress.

Figure 8:
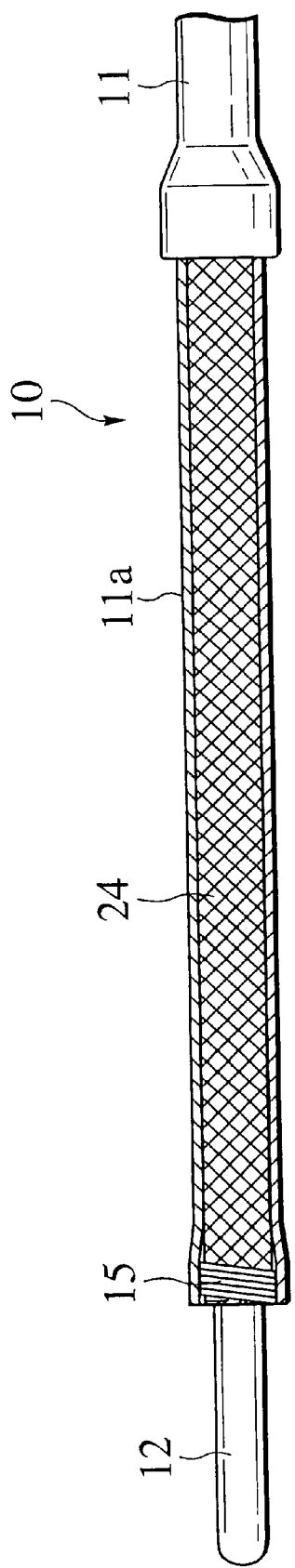
FIG. 8 is a side view corresponding to FIG. 3 and showing another example of a shaping member of the present invention.

In an alternative embodiment, a mesh tube 24 formed by metal wires as shown in FIG. 8 may be used as the shaping member instead of the coil 14.

Such a mesh tube 24, similar to the coil 14, has a structure which can impart a winding shape to the front end portion of the catheter main body 11. A preferred material for the mesh tube 14, includes the alloys and the like having super elasticity used for the coil 14.

Further, the shaping member, such as, the coil 14 and the mesh tube 24 may be inserted into the catheter main body 11 over the entire length of the catheter main body 11, although the coil 14 or the mesh tube 24 is provided only at the front end portion of the catheter main body 11 in the preferred embodiment. When the catheter 10 has such a structure, the catheter main body 11 is less likely to bend midway thus blocking the flow of the medication liquid.

What is claimed is:

1. A catheter comprising:
    a tube-shaped catheter main body;
    a shaping member provided at least at a front end portion of the catheter main body such that the shaping member can impart a winding shape to the front end portion of the catheter; and
    a cavity portion formed at an inner side of the shaping member.

2. A catheter according to claim 1, wherein the winding shape is a spiral shape.

3. A catheter according to claim 1, wherein the shaping member comprises a superelastic material.

4. A catheter according to claim 3, wherein the super elastic material includes at least one alloy selected from the group consisting of Ni—Ti alloy, Cu—Zn—X alloy (X=Al or Fe) and Ni—Ti—X (X=Fe, Cu, V or Co).

5. A catheter according to claim 1, wherein the shaping member comprises a coil.

6. A catheter according to claim 5, wherein the coil has a flat surface on a side of the cavity portion.

7. A catheter according to claim 5, wherein the shaping member takes on a double helical structure when the shaping member imparts the winding shape to the front end portion of the catheter main body.

8. A catheter according to claim 1, wherein the shaping member is formed by a mesh tube.

9. A catheter according to claim 1, wherein a portion of the front end portion of the catheter main body, to which portion the winding shape is imparted by the shaping member, is provided with holes.

10. A catheter according to claim 9, wherein the winding shape is a spiral shape and the holes are formed on the inner side of the spiral shape.

11. A catheter according to claim 1, wherein the catheter is inserted into a subject and the site where the catheter is retained has a diameter of the winding shape is set larger than that of the site where the catheter is retained.

* * * * *